United States Patent [19]

Gayer et al.

[11] Patent Number: 5,241,101

[45] Date of Patent: Aug. 31, 1993

[54] PESTICIDAL SUBSTITUTED OXIME ETHERS

[75] Inventors: Herbert Gayer, Monheim-Baumberg; Wolfgang Krämer, Burscheid; Stefan Dutzmann, Duesseldorf, all of Fed. Rep. of Germany

[73] Assignee: Bayer Aktiengesellschaft, Leverkusen, Fed. Rep. of Germany

[21] Appl. No.: 471,891

[22] Filed: Jan. 29, 1990

[30] Foreign Application Priority Data

Feb. 16, 1989 [DE] Fed. Rep. of Germany ....... 3904693

[51] Int. Cl.$^5$ .................. C07C 229/34; C07C 229/36
[52] U.S. Cl. ...................................... 560/35; 560/168; 549/23; 549/55; 549/401; 549/466
[58] Field of Search .................... 560/35, 168; 549/23, 549/55, 401, 466

[56] References Cited

U.S. PATENT DOCUMENTS 4,059,623 11/1977 Bellina .................................. 560/35

FOREIGN PATENT DOCUMENTS 0088326 9/1983 European Pat. Off. .
0178826 4/1986 European Pat. Off. .
2428070 1/1975 Fed. Rep. of Germany .
2029223 3/1980 United Kingdom .

Primary Examiner—José G. Dees
Assistant Examiner—B. Frazier
Attorney, Agent, or Firm—Sprung Horn Kramer & Woods

[57] ABSTRACT

Pesticidal substituted oxime ethers of the formula

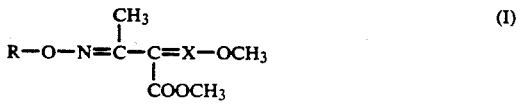

in which
R represents in each case unsubstituted or substituted alkyl, cycloalkyl, aryl or heterocyclyl and
X represents nitrogen or a CH group.

5 Claims, No Drawings

PESTICIDAL SUBSTITUTED OXIME ETHERS

The invention relates to new substituted oxime ethers, to several processes for their preparation, and to their use as pesticides.

It is known that certain 3-methoxyacrylic esters, such as, for example, the compound methyl 2-(2-methylphenyl)-3-methoxyacrylate, are fungicidally effective (cf., for example, EP 178,826).

However, the activity of these previously known compounds is not entirely satisfactory in all fields of use, in particular when low application rates and concentrations are used.

New substituted oxime ethers of the general formula (I)

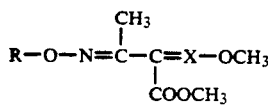

in which
R represents in each case unsubstituted or substituted alkyl, cycloalkyl, aryl or heterocyclyl and
X represents nitrogen or a CH group, have been found.

The compounds of the formula (I) can be present as geometric isomers or mixtures of isomers whose composition varies. The invention covers the pure isomers as well as the mixtures of isomers.

Furthermore, it has been found that the new substituted oxime ethers of the general formula (I)

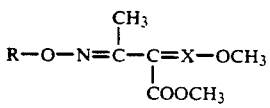

in which
R represents in each case unsubstituted or substituted alkyl, cycloalkyl, aryl or heterocycyl and
X represents nitrogen or a CH group,
are obtained when
(a) hydroxyoxime ethers of the formula (II)

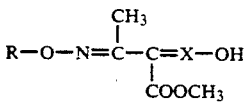

in which
R and X have the abovementioned meanings,
or their alkali metal enolate salts, are reacted with methylating agents of the formula (III)

in which
E represents an electron-withdrawing leaving group,
if appropriate in the presence of a diluent and if appropriate in the presence of a reaction auxiliary,
or when
(b) β-ketocarboxylic esters of the formula (IV)

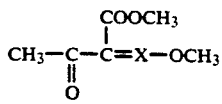

in which
X has the abovementioned meaning, are reacted with hydroxylamine derivatives of the formula (V)

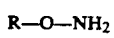

in which
R has the abovementioned meaning,
if appropriate in the presence of a diluent and if appropriate in the presence of a reaction auxiliary.

Finally, it has been found that the new substituted oxime ethers of the general formula (I) have a good activity against pests, in particular against phytopathogenic fungi.

Surprisingly, the substituted oxime ethers of the general formula (I) according to the invention show a considerably better activity against phytopathogenic fungi than the 3-methoxyacrylic esters which are known from the prior art, such as, for example, the compound methyl 2-(2-methylphenyl)-3-methoxyacrylate.

Formula (I) provides a general definition of the substituted oxime ethers according to the invention.

Unless defined otherwise, alkyl in the general formulae represents straight-chain or branched alkyl, preferably having 1 to 8, in particular 1 to 6 and especially 1 to 4, carbon atoms, with methyl, ethyl, n- and i-propyl, n-, i-, s- and t-butyl, pentyl and hexyl being mentioned as examples and as being preferred. The alkyl radicals, in turn, can carry one or more, preferably 1 to 3, in particular 1 or 2, identical or different substituents. Substituents which may be mentioned as examples and as being preferred are: alkyl having 1 to 4 carbon atoms, alkoxy having 1 to 4 carbon atoms, such as methoxy, ethoxy, n- and i-propoxy and n-, i-, s- and t-butoxy; alkylthio having 1 to 4 carbon atoms, such as methylthio, ethylthio, n- and i-propylthio and n-, i-, sand t-butylthio, and also preferably optionally substituted aryl having 6 to 10 carbon atoms, in particular optionally substituted phenyl.

Unless defined otherwise, cycloalkyl in the following preferably represents optionally substituted and/or in particular benzo-fused cycloalkyl having 3 to 7, in particular 5 or 6, carbon atoms.

Unless defined otherwise, aryl in the following preferably represents optionally substituted aryl having 6 to 10 carbon atoms, in particular optionally substituted phenyl.

Unless defined otherwise, heterocyclyl in the following preferably represents optionally substituted and/or in particular benzo-fused heterocyclyl having 2 to 6, in particular 4 or 5, carbon atoms and 1 to 3, in particular one hetero atom, such as nitrogen, oxygen and sulphur, in particular, however, thiazolyl, pyridinyl and pyrimidinyl.

The aryl radicals, the heterocyclyl radicals, the phenylene moiety of cycloalkyl radicals and the aryl substituents of alkyl radicals of the general formula can carry one or more, preferably 1 to 3, in particular 1 or 2, identical or different substituents. Substituents which may be mentioned as examples and as being preferred are: halogen, such as fluorine, chlorine, bromine and iodine, in particular fluorine, chlorine and bromine;

cyano; nitro; alkyl, alkoxy and alkylthio, preferably having 1 to 4 carbon atoms, and especially methyl, ethyl n- and i-propyl, n-, i-, s- and t-butyl, methoxy, ethoxy, n- and i-propoxy and methylthio; halogenoalkyl, halogenoalkoxy and halogenoalkylthio, preferably having 1 to 4 carbon atoms and 1 to 9 identical or different halogen atoms, in particular trifluoromethyl, trifluoromethoxy and trifluoromethylthio; alkoxycarbonyl and alkoximinoalkyl, preferably having 1 to 4 carbon atoms in the individual alkyl moieties, in particular methoxycarbonyl, ethoxycarbonyl, methoximinomethyl, ethoximinomethyl, methoximinoethyl and ethoximinoethyl; and phenyl which is optionally substituted, in particular monosubstituted to trisubstituted, by identical or different substituents from amongst halogen, in particular fluorine, chlorine and bromine, and alkyl and alkoxy having 1 to 4 carbon atoms, in particular methyl, ethyl and methoxy.

In the general formula, the cycloalkyl radicals can carry one or more, preferably 1 to 3, in particular or 2, substituents in the cycloalkyl moiety of an optionally benzo-fused cycloalkyl radical. Substituents which may be mentioned as examples and as being preferred are: halogen, such as fluorine, chlorine, bromine and iodine, and alkyl and alkoxy, preferably having 1 to 4 carbon atoms, in particular methyl, ethyl, methoxy and ethoxy.

Preferred compounds of the formula (I) are those in which

R represents straight-chain or branched alkyl having 1 to 8 carbon atoms, or represents straight-chain or branched alkoxyalkyl having 1 to 4 carbon atoms in each of the individual alkyl moieties, or represents straight-chain or branched alkylthioalkyl having 1 to 4 carbon atoms in each of the individual alkyl moieties, or represents aralkyl which has 1 to 6 carbon atoms in the straight-chain or branched alkyl moiety and 6 to 10 carbon atoms in the aryl moiety and which is unsubstituted or monosubstituted or polysubstituted by identical or different substituents, suitable substituents in the alkyl moiety being: straight-chain or branched alkyl having 1 to 4 carbon atoms and in each case straight-chain or branched alkoxy and alkylthio, each having 1 to 4 carbon atoms, and suitable substituents in the aryl moiety being: halogen, cyano, nitro, in each case straight-chain or branched alkyl, alkoxy and alkylthio, each having 1 to 4 carbon atoms, in each case straight-chain or branched halogenoalkyl, halogenoalkoxy and halogenoalkylthio, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl moieties, and also phenyl which is unsubstituted or monosubstituted or polysubstituted by identical or different substituents from amongst halogen and/or in each case straight-chain or branched alkyl or alkoxy, each having 1 to 4 carbon atoms; or represents cycloalkyl which has 3 to 7 carbon atoms and which is benzo-fused and/or unsubstituted or monosubstituted or polysubstituted by identical or different substituents, suitable substituents in the cycloalkyl moiety being: halogen and in each case straight-chain or branched alkyl and alkoxy, each having 1 to 4 carbon atoms, and suitable substituents in the benzo-fused moiety which may be present represents aryl which has 6 to 10 carbon atoms and being the abovementioned aryl substituents; or which is unsubstituted or monosubstituted or polysubstituted by identical or different substituents, suitable substituents being the abovementioned aryl substituents; or represents heterocyclyl which has 2 to 6 carbon atoms and 1 to 3 hetero atoms, in particular nitrogen, oxygen and/or sulphur, and which is benzo-fused and/or unsubstituted or monosubstituted or polysubstituted by identical or different substituents, suitable substituents in the heterocyclyl moiety and/or in the benzo-fused moiety which may be present being the abovementioned aryl substituents, and X represents nitrogen or a CH group.

Particularly preferred compounds of the formula (I) are those in which

R represents straight-chain or branched alkyl having 1 to 6 carbon atoms, or represents phenyl or phenylalkyl having 1 or 2 carbon atoms in the straight-chain or branched alkyl moiety, each of which is unsubstituted or monosubstituted to trisubstituted by identical or different substituents, suitable substituents in the alkyl moiety of phenylalkyl being: methyl, ethyl, n- or i-propyl, n-, i-, s- or t-butyl, methoxy, ethoxy, methylthio and ethylthio, suitable substituents of phenyl or in the phenyl moiety of phenylalkyl being: fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl, ethoximinoethyl and phenyl which is unsubstituted or monosubstituted to trisubstituted by identical or different substituents from amongst fluorine, chlorine, bromine, methyl, methoxy and/or ethyl; or represents a radical of the formula

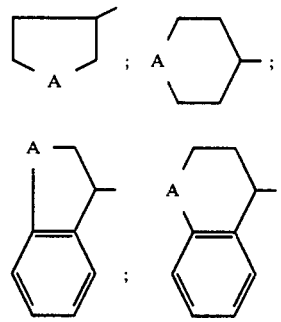

where

A in each case represents oxygen, sulphur or a CH$_2$ group, which radical is unsubstituted or monosubstituted to pentasubstituted by identical or different substituents, suitable substituents in the alicyclic rings in each case being: methyl, ethyl, methoxy and ethoxy, and suitable substituents in the phenylene moiety in each case being the abovementioned phenyl substituents, and X represents nitrogen or a CH group.

Very particularly preferred compounds of the formula (I) are those in which

R represents a radical of the formula

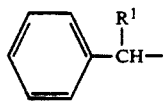

where
R[1] represents hydrogen, methyl, ethyl, n- or i-propyl, or represents methoxymethyl, ethoxymethyl or methylthiomethyl,
which radical is unsubstituted or monosubstituted to trisubstituted in the phenyl moiety by identical or different substituents, suitable substituents in the phenyl moiety in each case being: fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, methoxycarbonyl, ethoxycarbonyl, methoximinomethyl, ethoximinomethyl, methoximinoethyl, ethoximinoethyl and phenyl which is unsubstituted or monosubstituted to trisubstituted by identical or different substituents from amongst fluorine, chlorine, bromine, methyl, methoxy and/or ethyl, and X represents nitrogen or a CH group.

Other very particularly preferred compounds of the formula (I) are those in which
R represents a radical of the formula

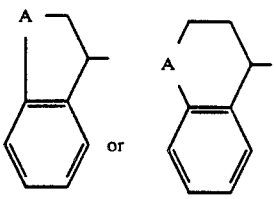

where
A in each case represents oxygen, sulphur or a CH$_2$ group,
each of these radicals being unsubstituted or monosubstituted to trisubstituted in the phenylene moiety by identical or different substituents, suitable substituents in the phenylene moiety in each case being: fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, methoxycarbonyl, ethoxycarbonyl, methoximinomethyl, ethoximinomethyl, methoximinoethyl, ethoximinoethyl and phenyl which is unsubstituted or monosubstituted to trisubstituted by identical or different substituents from amongst fluorine, chlorine, bromine, methyl, methoxy and/or ethyl, and X represents nitrogen or a CH group.

The following substituted oxime ethers of the general formula (I) may be mentioned individually in addition to the compounds mentioned in the Preparation Examples:

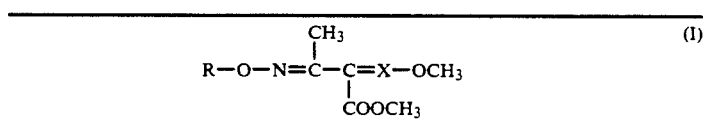

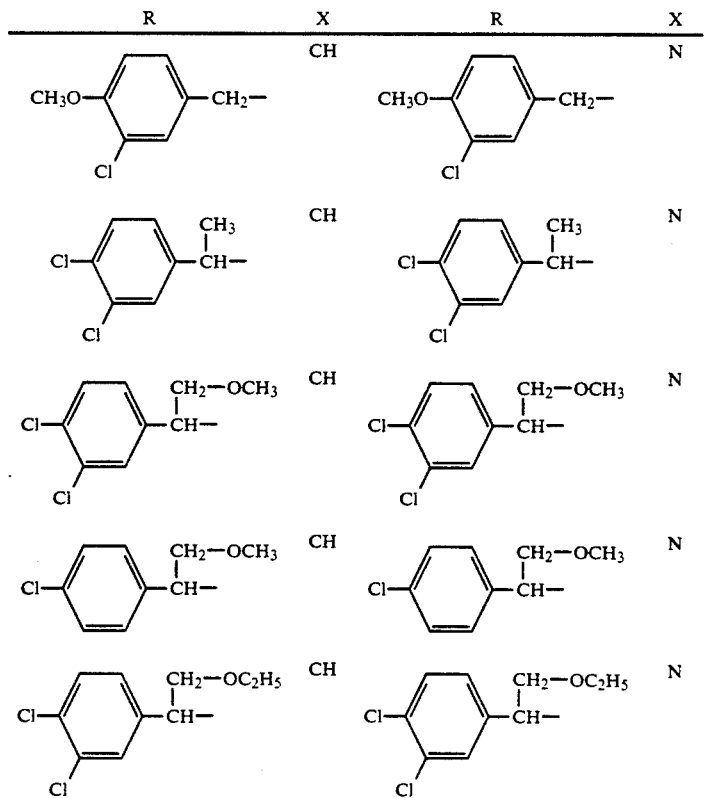

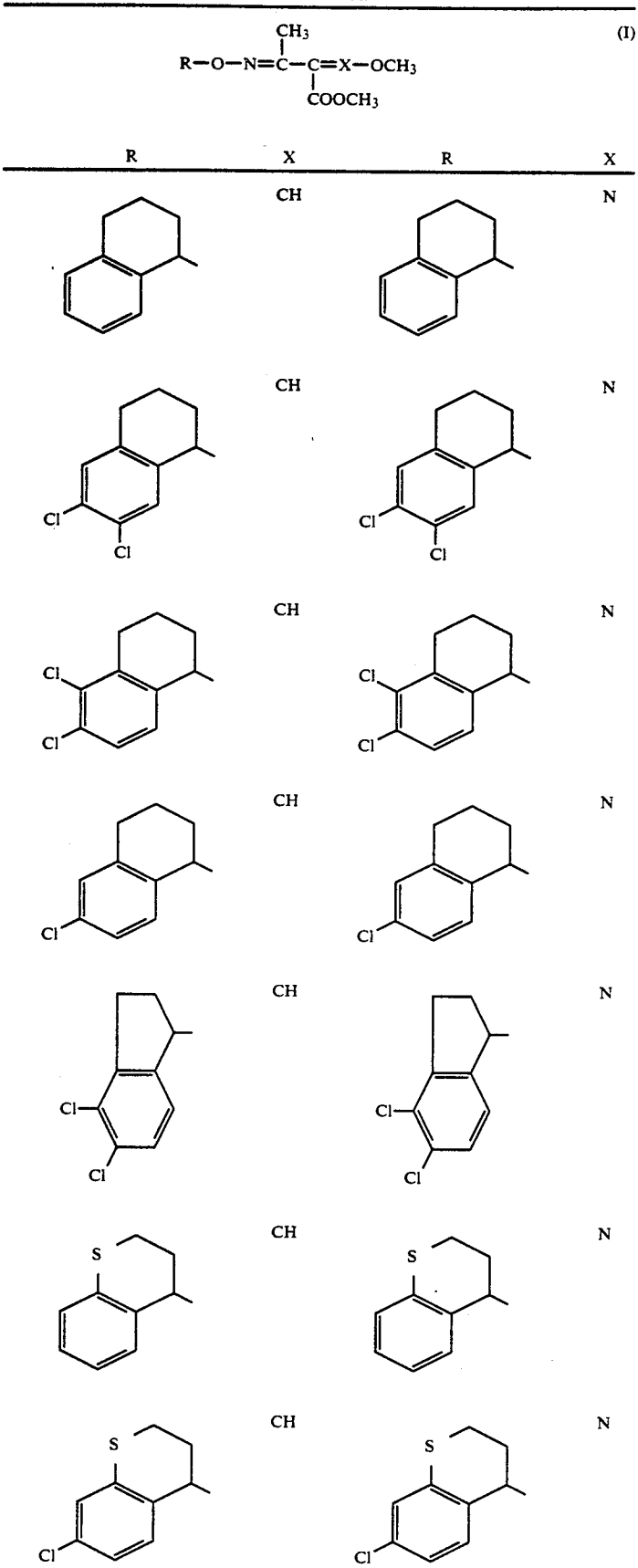

-continued
$$R-O-N=\underset{\underset{COOCH_3}{|}}{\overset{\overset{CH_3}{|}}{C}}-C=X-OCH_3 \qquad (I)$$
| R | X | R | X |
|---|---|---|---|
| 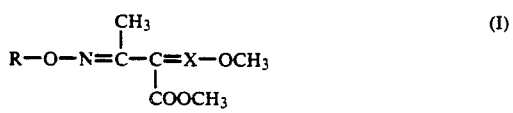 2-(methylthio)benzyl | CH | 2-(methylthio)benzyl | N |
| chroman-4-yl | CH | chroman-4-yl | N |
| 6-chlorochroman-4-yl | CH | 6-chlorochroman-4-yl | N |
| 2,3-dihydrobenzofuran-3-yl | CH | 2,3-dihydrobenzofuran-3-yl | N |
| 2-phenylthiazol-4-yl | CH | 2-phenylbenzothiazol-2-yl | CH |
| 2-(4-chlorophenyl)thiazol-4-yl | CH | 2-phenylpyrimidin-4-yl | CH |

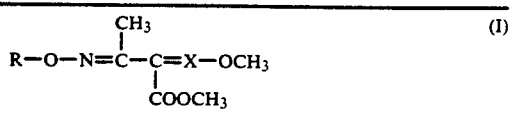

| R | X | R | X |
|---|---|---|---|
| 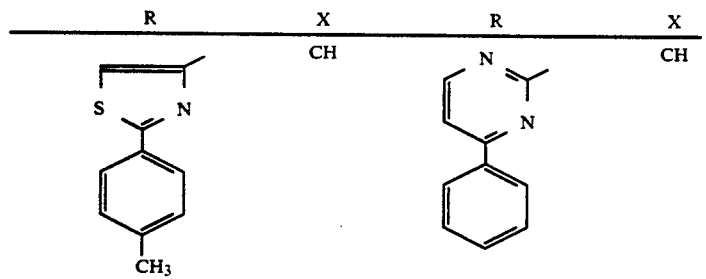 | CH | | CH |

If, for example, methyl 3-benzyloximino-2-hydroxymethylidenobutyrate and dimethyl sulphate are used as starting materials, the course of the reaction of process (a) according to the invention may be prepresented by the following equation:

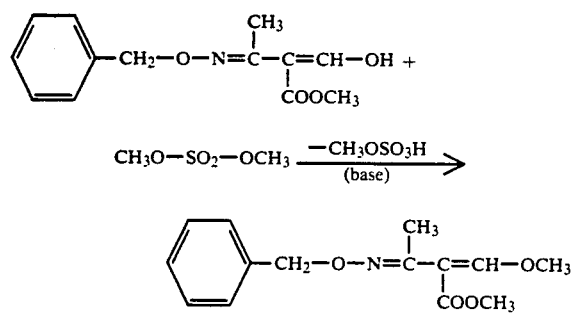

If, for example, methyl 2-methoxyimino-3-oxobutyrate and 0-(1-phenylethyl)-hydroxylamine are used as starting materials, the course of the reaction of process (b) according to the invention may be represented by the following equation:

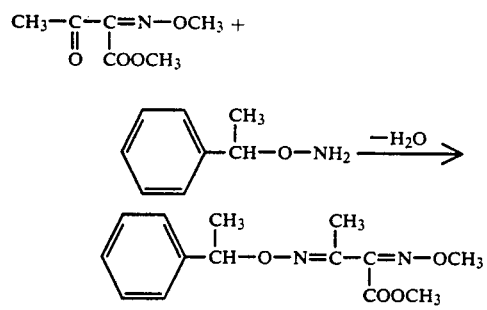

Formula (II) provides a general definition for the hydroxyoxime ethers required as starting materials for carrying out process (a) according to the invention. In this formula (II), R and X preferably represent those radicals which have already been mentioned in connection with the description of the substances of the formula (I) according to the invention as being preferred for these substituents.

The hydroxyoxime ethers and their alkali metal enolate salts of the formula (II) were hitherto unknown and are likewise a subject of the invention; they are obtained when methyl acetoacetate, of the formula (VI),

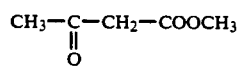

is reacted with hydroxy-lamine derivatives of the formula (V)

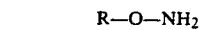

in which
R has the abovementioned meaning,
if appropriate in the presence of a diluent, such as, for example, toluene, and if appropriate in the presence of a water-binding reaction auxiliary, such as, for example, a molecular sieve, at temperatures between 0° C. and 180° C. [cf. also in this context, the reaction conditions for carrying out the analogous process (b) according to the invention], and the resulting methyl hydroxyiminobutyrate, of the formula (VII),

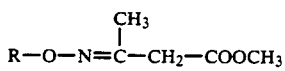

in which
R has the abovementioned meaning
is either
(α) initially reacted with dimethylformamide dimethyl acetal at temperatures between 50° C. and 180° C., if appropriate in the presence of a diluent such as, for example, dimethylformamide or toluene, to give the enamines of the formula (VIII)

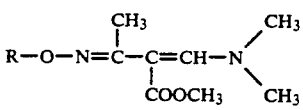

in which R has the abovementioned meaning, and these are reacted in a subsequent reaction step (or without isolation, directly in a one-pot process) with a dilute aqueous mineral acid, such as, for example, hydrochloric acid, at temperatures between 20° C. and 100° C., if appropriate in the presence of a diluent, such as, for example, dimethylformamide or acetone, or (β) reacted with methyl formate at temperatures between 0° C. and 40° C., if appropriate in the presence of a diluent, such as, for example, dimethylformamide or toluene, and if appropriate in the presence of a basic reaction auxiliary, such as, for example, sodium hydride, or (γ) nitrosated with an alkyl nitrite, such as, for example, isopentyl nitrite, at temperatures between 0° C. and 60° C., if appropriate in the presence of a diluent, such as, for example, methanol, and if appropriate in the presence of a reaction auxiliary, such as, for example, sodium methoxide.

Methyl hydroxyiminobutyrates of the formula (VII) and enamines of the formula (VIII) were hitherto unknown and are also the subject of the invention.

Formula (III) provides a general definition of the methylating agents required as starting materials for carrying out process (a) according to the invention. In this formula (III), E preferably represents one of the leaving groups customary in the case of methylating agents, such as, for example, bromine, iodine, methoxysulphonyloxy or p-toluenesulphonyloxy.

The methylating agents of the formula (III) are generally known compounds of organic chemistry.

Formula (IV) provides a general definition of the β-ketocarboxylic esters required as starting materials for carrying out process (b) according to the invention, and they are described, for example, in PCT Int. Appl. WO 86/1202; U.S. Pat. No. 4,555,517; J. Chem. Soc., Perkin Trans. 1, 464–471 ([1979]; J. Antibiotic, 34, 160–170 [1981]; JP 53/34,795; DE-OS (German Published Specification) 2,805,655; CH 637,141, or they can be obtained in analogy to known processes.

Formula (V) provides a general definition of the hydroxylamine derivatives required as starting materials for carrying out process (b) according to the invention and for the synthesis of the precursors of the formulae (II), (VII) and (VIII).

In this formula (V), R preferably represents those radicals which have already been mentioned in connection with the description of the substances of the formula (I) according to the invention as being preferred for these substituents.

The hydroxylamine derivatives of the formula (V) are generally known compounds of organic chemistry, or they can be obtained in analogy to generally known processes (cf., for example, GB 1,042,191; Tetrahedron Lett. 23, 2955-2956 [1982]; DE-OS (German Published Specification) 3,615,473)

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride; ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If appropriate, process (a) according to the invention can also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethyl-ammonium methylsulphate, dimethyl-$C_{12}$/$C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable reaction auxiliary. Suitable reaction auxiliaries are all inorganic The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline,pyridine,N,N-dimethylaminopyridine, diazabicyclooctane (DABCO), diazabicyclononene (DBN) or diazabicycloundecene (DBU) are preferably used.

When carrying out process (a) according to the invention, the reaction temperatures can be varied within a substantial range. In general, the process is carried out at temperatures between −20° C. and 200° C., preferably at temperatures between 0° C. and 180° C.

For carrying out process (a) according to the invention, 1.0 to 5.0 moles, preferably 1.0 to 1.5 moles, of methylating agent of the formula (III) and, if appropriate, 1.0 to 5.0 moles, preferably 1.0 to 2.0 moles, of reaction auxiliary are generally employed per mole of hydroxyoxime ether of the formula (II) or a corresponding alkali metal enolate salt. In this context, it is also possible to prepare the hydroxyoxime ethers of the formula (II) or their corresponding alkali metal enolate salts, which are to be used as starting compounds of the formula (II), in a preceding reaction directly in the reaction vessel, and to react the products with the methylating agent of the formula (III) without isolation from the reation mixture (one-pot reaction). The reaction is carried out and the reaction products are worked up and isolated by generally customary methods (cf. also the Preparation Examples).

Suitable diluents for carrying out process (b) according to the invention are inert organic solvents or their mixtures with water. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofurane, ethylene glycol dimethyl ether or ethylene glycol diethyl ether, nitriles, such as acetoLe nitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, alcohols, such as methanol, ethanol, propanol or butanol, or their mixtures with water.

If appropriate, process (b) according to the invention can be carried out in the presence of a suitable water-binding reaction auxiliary. Suitable reaction auxiliaries are all customary water-binding agents which are inert under the reaction conditions and which can easily be separated from the reaction products. It is particularly preferred to remove any water which is liberated during the reaction by azeotropic distillation with the aid of a water separator.

When carrying out process (b) according to the invention, the reaction temperatures can be varied within a substantial range. In general, the process is carried out at temperatures between 20° C. and 200° C., preferably at temperatures between 60° C. and 180° C.

For carrying out process (b) according to the invention, 1.0 to 3.0 moles, preferably 1.0 to 1.2 moles, of hydroxylamine derivative of the formula (V) and, if appropriate, 1.0 to 50.0 moles, preferably 1.0 to 5.0 moles, of reaction auxiliary are generally employed per mole of β-ketocarboxylic ester of the formula (IV). It is also possible to employ the hydroxylamine derivatives of the formula (V), which are to be used as starting compounds of the formula (V), in the form of suitable acid addition salts, such as, for example, hydroLe chlorides. In this event, the process is customarily carried out in the presence of equivalent amounts of a suitable acid-binding agent. Acid-binding agents which are preferably employed are alkali metal carbonates or alkali metal acetates, such as, for example, sodium carbonate, potassium carbonate or sodium acetate.

The reaction is carried out and the reaction products are worked up and isolated by generally customary methods (cf. also the Preparation Examples).

The substituted oxime ethers of the formula (I) which can be obtained with the aid of processes (a) or (b) according to the invention are usually obtained as mixtures of stereoisomers whose composition varies. These mixtures of stereoisomers can either be used as such according to the invention or separated into the individual components with the aid of customary separation methods. Suitable separation methods in this context are, in particular, liquid chromatography or high-vacuum distillation.

The products are characterized with the aid of the melting point or the proton nuclear resonance spectra.

The active substances according to the invention show a powerful action against pests and can be employed in practice for combating undesired harmful organisms. The active substances are suitable for use as plant-protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, Septoria nodorum;

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases, such as, for example, against the pathogen causing net blotch of barley (*Pyrenophora teres*) or against the pathogen causing glume blotch of wheat (*Leptosphaeria nodorum*) or against the pathogen causing powdery mildew of cereals (*Erysiphe graminis*) and also for combating rice diseases, such as, for example, against the pathogen causing rice blast disease (*Pyricularia oryzae*) or against the pathogen causing rice stem disease (*Pellicularia sasakii*) or for combating diseases in fruit and vegetable growing, such as, for example, against the pathogen causing apple scab (*Venturia inaequalis*), or against Oomycetes.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide, Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

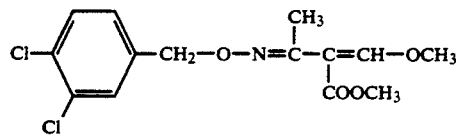

(Process a)

To 7.1 g (0.0223 mol) of methyl 3-(3,4-dichlorobenzyloximino)-2-hydroxymethylidenebutyrate in 23 ml of dimethylformamide there are added in succession 6.2 g (0.0449 mol) of potassium carbonate and then, dropwise and with ice-cooling, 2.9 g (0.023 mol) of dimethyl sulphate, the reaction mixture is subsequently stirred for 2 hours at room temperature and then poured into 140 ml of ice-water, the mixture is extracted three times using 70 ml of diethyl ether each time, and the combined organic phases are washed with 140 ml of water, dried over sodium sulphate and concentrated in vacuo.

This gives 6.8 g (92 % of theory) of methyl 3-(3,4-dichlorobenzyloximino)-2-methoxymethylidenebutyrate as a mixture of isomers, which can separated by chromatography on silica gel (eluent: diethyl ether/petroleum ether 1:1) into 2 fractions and distilled under a high vacuum.

Isomer A: 2.7 g (36% of theory)
$^1$H-NMR (CDCl$_3$/tetramethylsilane): δ=2.02 (3H); 3.71 (3H); 3.88 (3H); 5.02 (2H); 7.11 (1H); 7.33–7.42 (2H); 7.31 (1H) ppm.

Isomer B: 3.7 g (49 % of theory)
$^1$H-NMR (CDCl:/tetramethylsilane): δ=2.04 (3H); 3.72 (3H); 3.87 (3H); 5.12 (2H); 7.2 (1H); 7.33–7.48 (2H); 7.44 (1H) ppm.

Alternative preparation process (Process a—one-pot variant)

To a suspension of 4.1 g (0.137 mol) of sodium hydride (80 per cent pure in paraffin) in 70 ml of dimethylformamide there is added dropwise with stirring at room temperature a solution of 20 g of methyl 3-(3,4-dichlorobenzyloximino)-butyrate in 41.4 g (0.689 mol) of methyl formate, the mixture is subsequently stirred for 12 hours at room temperature, and 6.6 g (0.069 mol) of methanesulphonic acid are then added successively at 0° C. with stirring and cooling, followed by 9.5 g (0.069 mol) of potassium carbonate and finally by 8.7 g (0.069 mol) of dimethyl sulphate, likewise dropwise and with stirring and cooling. When the addition is complete, the reaction mixture is stirred for 2 hours at room temperature and then poured into water, the mixture is extracted several times using ether, and the ether phase is dried over sodium sulphate and concentrated in vacuo, and the residue is purified by chromatography on silica gel (eluent: ether/petroleum ether 1:1).

This gives 10.1 g (44 % of theory) of methyl 3-(3,4 dichlorobenzyloximino)-2-methoxymethylidenebutyrate as a mixture of isomers.

Example 2

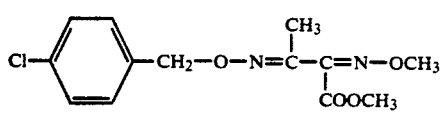

(Process b)

4.3 g (0.027 mol) of methyl 2-methoximinoacetoacetate (cf., for example, DE-OS (German Published Specification) 2,805,590) are refluxed together with 4.3 g (0.027 mol) of 0-(4-chlorobenzyl)-hydroxylamine (cf., for example, J. med. Chem. 10, 556–564 [1967]) in 30 ml of toluene for 60 minutes. The solvent is subsequently distilled off. The residue is subjected to high-vacuum distillation using a bulb tube (boiling point 100° C. at 0.2 mbar).

This gives 5.5 g (68 % of theory) of methyl 3-(4-chlorobenzyloximino)-2-methoximino-butyrate as a mixture of two isomers A and B in the ratio 40:60.

Isomer A:

$^1$H-NMR (CDCl$_3$/tetramethylsilane): δ=2.09 (3H); 3.5 (3H); 3.99 (3H); 5.02 (2H); 7.2–7.45 (4H) ppm.

Isomer B $^1$H-NMR (CDCl$_3$/tetramethylsilane):

2.05 (3H); 3.82 (3H); 3.99 (3H); 5.12 (2H), 7.2–7.45 (4H)

The following substituted oxime ethers of the general formula (I)

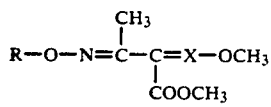

are obtained in a corresponding manner and following the general preparation instructions:

| Ex. No. | R | X | $^1$H-NMR*) |
|---|---|---|---|
| 3 | 4-Cl-C$_6$H$_4$-CH$_2$- | CH | 2.0; 3.6; 3.8; 5.1; 7.2–7.4 |
| 4 | 2-Cl-C$_6$H$_4$-CH$_2$- | CH | 2.1; 3.6; 3.85; 5.3; 7.1–7.5 |
| 5 | 4-CH$_3$-C$_6$H$_4$-CH$_2$- | CH | 2.2; 3.7; 3.8; 5.1; 7.1–7.5 |
| 6 | 3,4-Cl$_2$-C$_6$H$_3$-CH$_2$- | N | 2.1; 3.7; 4.0; 5.1; 7.1–7.2 |
| 7 | 4-CH$_3$-C$_6$H$_4$-CH$_2$- | N | 2.1; 3.6; 4.0; 5.05; 7.1–7.3 |
| 8 | 2-Cl-C$_6$H$_4$-CH$_2$- | N | 2.1; 3.7; 4.0; 5.25; 7.2–7.4 |
| 9 | 2,3-Cl$_2$-C$_6$H$_3$-CH$_2$- | N | 2.05; 3.6; 3.95; 5.4; 7.15–7.5 |

*)The $^1$H-NMR spectra were recorded in deuterochloroform (CDCl$_3$) using tetramethylsilane (TMS) as the internal standard. The chemical shift is indicated as at δ-value in ppm.

PREPARATION OF THE STARTING COMPOUNDS

Example II-1

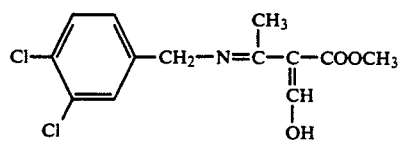

To 11.15 g (0.0323 mol) of methyl 3-(3,4-dichlorobenzyloximino)-2-dimethylaminomethylidenebutyrate in 38 ml of dimethylformamide there are added at room temperature and with cooling and stirring 18 ml (0.036 mol) of 2-normal aqueous hydrochloric acid in such a way that the internal temperature of the reaction mixture does not exceed 35° C., the mixture is allowed to stand for 10 minutes and then poured into 200 ml of ice-water, the mixture is extracted 3 times using 100 ml of diethyl ether each time, the combined organic phases are washed in succession with 200 ml of water and 100 ml of 2-normal hydrochloric acid, dried over sodium sulphate and concentrated in vacuo, and the residue is recrystallized from n-hexane.

This gives 7.8 g (76 % of theory) of methyl 3-(3,4-dichlorobenz-vloximino)-2-hydroxy-methylidenebutyrate of melting point 63° C.–65° C.

Example II-2

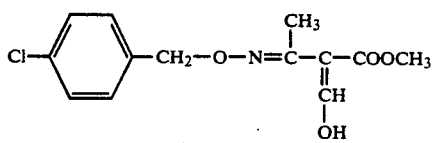

To a suspension of 1.2 g (0.04 mol) of sodium hydride in 20 ml of dimethylformamide there is added dropwise at room temperature and with stirring a solution of 5.1 g (0.02 mol) of methyl 3-(4-chlorobenzyloximino)butyrate in dissolved form, the mixture is subsequently stirred for 4 hours at room temperature, then acidified using 2-normal aqueous hydrochloric acid and extracted several times using ethyl acetate, the organic phase is dried over sodium sulphate and concentrated in vacuo, and the residue is purified by chromatography on silica gel (eluent: cyclohexane/ethyl acetate 2:1).

This gives 3.7 g (65% of theory) as an oily mixture of 2 stereoisomers.

$^1$H-NMR (CDCl$_3$/tetramethylsilane): δ=2.04; 2.3 (3H); 3.72; 3.8 (3H); 5.06 (2H) 7.2–7.4 (4H); 8.12 (1H; 11.8; 13.1 (1H) ppm.

The following hydroxyoxime ethers of the general formula (II) are obtained in a corresponding manner and following the general preparation instructions:

$$R-O-N=\overset{\overset{CH_3}{|}}{C}-\underset{\underset{COOCH_3}{|}}{C}=X-OH$$

| Ex. No. | R | X | $^1$H-NMR*) |
|---|---|---|---|
| II-3 | 2-Cl-C$_6$H$_4$-CH$_2$- | CH | 2.34: 3.72: 5.20: 7.1–7.5: 8.17 |
| II-4 | 4-CH$_3$-C$_6$H$_4$-CH$_2$- | CH | 2.30: 2.35: 3.70: 3.79; 5.0; 7.1–7.3: 8.22: 13.4 |
| II-5 | 2,6-Cl$_2$-C$_6$H$_3$-CH$_2$- | CH | 2.27: 3.7: 5.38: 7.1–7.4: 8.13: 13.0 |
| II-6 | 3,4-Cl$_2$-C$_6$H$_3$-CH$_2$- | CH | 2.3: 3.7: 5.16: 7.2–7.4: 8.1: 12.95 |

*)The $^1$H-NMR spectra were recorded in deuterochloroform (CDCl$_3$) using tetramethylsilane (TMS) as the internal standard. The chemical shift is indicated as δ-value in ppm.

Example VIII-1

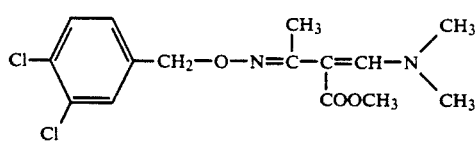

20 g (0.069 mol) of methyl 3-(3,4-dichloro-benzyloximino)-butyrate are refluxed for 4 hours together with 12.3 g (0.103 mol) of N,N-dimethylformamide dimethyl acetal in 35 ml of toluene, during which process any methanol which is liberated is continuously distilled off. The mixture is subsequently concentrated in vacuo, and the residue is subjected to high-vacuum distillation using a bulb tube (b.p. 180°–190° C. at 0.1 mbar).

This gives 23 g (97 % of theory) of methyl 3-(3,4-dichlorobenzyloximino)-2-dimethylaminomethylidenebutyrate as an oily mixture of 4 stereoisomers.

$^1$-NMR (CDCl$_3$/tetramethylsilane): δ=2.08 (3H); 2.78; 2.88 (6H); 3.68 (3H); 5.02; 5.08 (2H); 7.0–7.5 (4H) ppm.

The following substituted enamines of the general formula (VIII) are obtained in a corresponding manner and following the general preparation instructions:

$$R-O-N=\overset{\overset{CH_3}{|}}{C}-\underset{\underset{COOCH_3}{|}}{C}=CH-N\overset{CH_3}{\underset{CH_3}{\diagdown}}$$

| Ex. No. | R | $^1$H-NMR*) |
|---|---|---|
| VIII-2 | 4-Cl-C$_6$H$_4$-CH$_2$- | 2.04: 2.75: 2.78: 3.64: 5.01: 5.1: 7.2–7.4 |
| VIII-3 | 2,4-Cl$_2$-C$_6$H$_3$-CH$_2$- | 2.1: 2.44: 3.7: 5.12: 5.20: 7.1–7.5 |

*)The $^1$H-NMR spectra were recorded in deuterochloroform (CDCl$_3$) using tetramethylsilane (TMS) as the internal standard. The chemical shift is indicated as δ-value in ppm.

Example VII-1

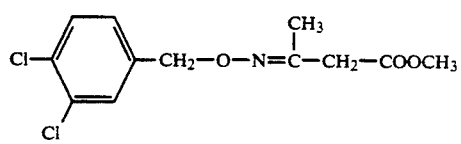

19.2 g (0.1 mol) of 0-(3,4-dichlorobenzyl)hydroxylamine (cf., for example, DE-OS (German Published Specification) 3,116,888) and 11.6 g (0.1 mol) of methyl acetoacetate are refluxed in 100 ml of toluene for 2 hours, in a water separator For working-up, the mixture is cooled and concentrated in vacuo, and the residue is distilled under a high vacuum.

This gives 21.6 g (74.4 % of theory) of methyl 3-(3,4-dichlorobenzyloximino)-butyrate of boiling point 142° C. to 152° C. at 0.3 mbar.

The following is obtained in a corresponding manner:

Example VII-2:

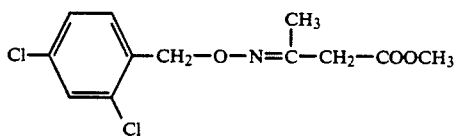

Use Example

In the Use Example which follows, the compound listed below was used as the comparison substance:

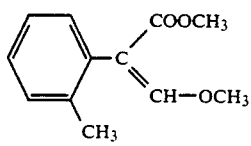

Example A

*Pyrenophora teres* test (barley)/protective/curative

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

At an exemplary active compound concentration of 0.025 % by weight, the compound of Preparation Example 1 shows a degree of effectiveness of 100 %. The compound of the prior art does not show any effect.

It will be understood that the specification and examples are illustrative but not limitative of the present invention and that other embodiments within the spirit and scope of the invention will suggest themselves to those skilled in the art.

What is claimed is:

1. An oxime ether of the formula

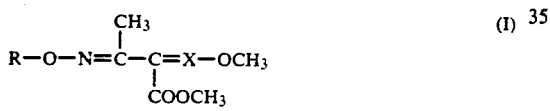

R represents straight-chain or branched alkyl having 1 to 8 carbon atoms, or represents straight-chain or branched alkoxyalkyl having 1 to 4 carbon atoms in each of the individual alkyl moieties, or represents straight-chain or branched alkylthioalkyl having 1 to 4 carbon atoms in each of the individual alkyl moieties, or represents aralkyl which has 1 to 6 carbon atoms in the straight-chain or branched alkyl moiety and 6 to 10 carbon atoms in the aryl moiety and which is unsubstituted or monosubstituted or polysubstituted on the alkyl moiety by identical or different substituents selected from the group consisting of straight-chain or branched alkyl having 1 to 4 carbon atoms and in each case straight-chain or branched alkoxy and alkylthio, each having 1 to 4 carbon atoms, and suitable substituents in the aryl moiety by halogen, cyano, nitro, in each case straight-chain or branched alkyl, alkoxy and alkylthio, each having 1 to 4 carbon atoms, in each case straight-chain or branched halogenoalkyl, halogenoalkoxy and halogenoalkylthio, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl moieties, or also phenyl which is unsubstituted or monosubstituted or polysubstituted by identical or different substituents from the group consisting of halogen and in each case straight-chain or branched alkyl and alkoxy, each having 1 to 4 carbon atoms; or represents cycloalkyl which has 3 to 7 carbon atoms and which is benzo-fused and/or unsubstituted or monosubstituted or polysubstituted in the cycloalkyl moiety by identical or different substituents selected from the group consisting of halogen and in each case straight-chain or branched alkyl and alkoxy, each having 1 to 4 carbon atoms, and optionally substituted in the benzo-fused moiety by the abovementioned optional aryl substituents; or represent aryl which has 6 to 10 carbon atom and which is unsubstituted or monosubstituted or identically or differently polysubstituted by the abovementioned aryl substituents; or represents a radial of the formula

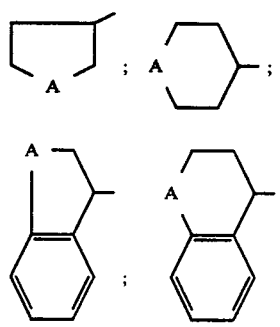

where

A in each case represents oxygen, sulphus or a $CH_2$ group, which radical is unsubstituted or monosubstituted to pentasubstituted by identical or different substituents, when present substituents in the alicyclic rings in each case being selected from the group of methyl, ethyl, methoxy and ethoxy, and when present substituents in the phenylene moiety in each case being the abovementioned aryl substituents, and X represents nitrogen or a CH group.

2. An oxime ether according to claim 1, in which

R represents straight-chain or branched alkyl having 1 to 6 carbon atoms, or represents phenyl or phenylalkyl having 1 or 2 carbon atoms in the straight-chain or branched alkyl moiety, each of which is unsubstituted or monosubstituted to trisubstituted by identical or different substituents, when present substituents in the alkyl moiety of phenylalkyl being selected from the group consisting of methyl, ethyl, n- or i-propyl, n-, i-, s- or t-butyl, methoxy, ethoxy, methylthio and ethylthio, when present substituents of phenol or in the phenyl moiety of phenylalkyl being selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluormethylthio, methoxycarbonyl, ethoxycarbonyl, methoximinomethyl, ethoximinomethyl, methoximinoethyl, ethoximinoethyl and phenyl which is unsubstituted or monosubstituted to trisubstituted by identical or different substituents selected from the group consisting of fluorine, chlorine, bromine, methyl, aethoxy and ethyl; or represents a radical of the formula

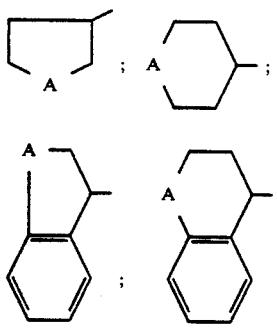

where

A in each case represents oxygen, sulphur or a CH$_2$ group, which is unsubstituted or monosubstituted to pentasubstituted by identical or different substitutents, when present substituents in the alicyclic rings in each case being selected from the group consisting of methyl, ethyl, methoxy and ethoxy, and when present substituents in the phenylene moiety in each case being the abovementioned phenyl substituents, and X represents nitrogen or a CH group.

3. An oxime ether according to claim 1, in which R represents a radical of the formula

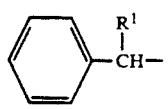

where

R$^1$ R$^1$ represents hydrogen, methyl, ethyl, n- or i-propyl, or represents methoxymethyl, ethoxymethyl or methylthiomethyl, which radical is unsubstituted or monosubstituted to trisubstituted in the phenyl moiety by identical or different substituents selected from the group consisting of fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, methoxycarbonyl, ethoxycarbonyl, methoximinomethyl, ethoximinomethyl, methoximinoethyl, ethoximinoethyl and phenyl which is unsubstituted or monosubstituted to trisubstituted by identical of different substituents selected from the group consisting of fluorine, chlorine, bromine, methyl, methoxy and ethyl, and X represents nitrogen or a CH group.

4. An oxime ether according to claim 1, in which R represents a radical of the formula

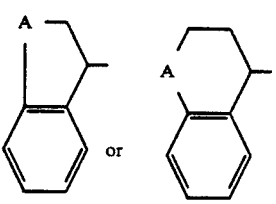

where

A in each case represents oxygen, sulphur or a CH$_2$ group, each of these radicals being unsubstituted or monsubstituted to trisubstituted in the phenylene moiety by identical or different substituents selected from the group consisting of luorine, chlorine, bromine, methyl, ethyl, n- or i-propyl, n-, i, s-, or t-butyl, methoxy, ethoxy, n- or i-propoxy, methylthio, trifluoromethyl, trifluoromethoxy, methoxycarbonyl, ethoxycarbonyl, methoximinomethyl, ethoximinomethyl, methoximinoethyl, ethoximinoethyl and phenyl which is unsubstituted or monosubstituted to trisubstituted by identical or different substituents from the group consisting of fluorine, chlorine, bromine, methyl, methoxy and ethyl, and X represents nitrogen or a CH group.

5. A compound according to claim 1, wherein such compound is methyl 3-(3,4-dichlorobenzyloximino)-2-methoxymethylidenebutyrate of the formula

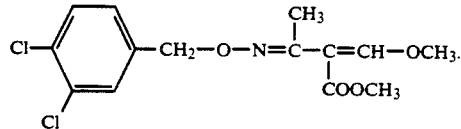

* * * * *

UNITED STATES PATENT AND TRADEMARK OFFICE
CERTIFICATE OF CORRECTION

PATENT NO. : 5,241,101

DATED : August 31, 1993

INVENTOR(S) : Herbert Gayer, et al.

It is certified that error appears in the above-identified patent and that said Letters Patent is hereby corrected as shown below:

| | |
|---|---|
| Col. 23, Line 39 | After formula insert --in which-- |
| Col. 23, Lines 55-56 | Delete "suitable substituents" and substitute --optionally substituted-- |
| Col. 24, Line 11 | Delete "represent" and substitute --represents-- |
| Col. 24, Line 32 | Delete "Sulphus" and substitute ----sulphur-- |
| Col 24, Line 37 | After "group" insert --consisting-- |
| Col. 24, Lines 48-49 | After "moiety" delete "each of which is" and substitute --said phenyl or phenyl-alkyl radicals being-- |
| Col. 24, Line 55 | Delete "phenol" and substitute --phenyl-- |
| Col. 24, Next to last line | Delete "aethoxy" and substitute --methoxy-- |
| Col. 25, Line 19 | After "which" insert --radical-- |

UNITED STATES PATENT AND TRADEMARK OFFICE
CERTIFICATE OF CORRECTION

PATENT NO. : 5,241,101
DATED : August 31, 1993
INVENTOR(S) : Herbert Gayer, et al.

It is certified that error appears in the above-identified patent and that said Letters Patent is hereby corrected as shown below:

| | |
|---|---|
| Col. 25, Line 37 | Delete "R" (first occurrence) |
| Col. 26, Line 2 | Delete "of" and substitute --or-- |
| Col. 26, Line 25 | Delete "luorine" and substitute --fluorine-- |

Signed and Sealed this

Twenty-fifth Day of April, 2000

*Attest:*

Q. TODD DICKINSON

*Attesting Officer*      *Director of Patents and Trademarks*